(12) United States Patent
Yu et al.

(10) Patent No.: US 11,703,432 B2
(45) Date of Patent: Jul. 18, 2023

(54) IN-SITU TEST DEVICE FOR SURROUNDING ROCK STRENGTH OF BOLT SUPPORTED ROADWAY AND METHOD THEREOF

(71) Applicant: SHANDONG UNIVERSITY OF SCIENCE AND TECHNOLOGY, Qingdao (CN)

(72) Inventors: Fenghai Yu, Qingdao (CN); Xuerui Yang, Qingdao (CN); Yunliang Tan, Qingdao (CN); Qiang Ren, Qingdao (CN); Kai Zhou, Qingdao (CN); Chuang Zhang, Qingdao (CN); Pan Du, Qingdao (CN); Qingduo Wang, Qingdao (CN)

(73) Assignee: SHANDONG UNIVERSITY OF SCIENCE AND TECHNOLOGY, Qingdao (CN)

( * ) Notice: Subject to any disclaimer, the term of this patent is extended or adjusted under 35 U.S.C. 154(b) by 0 days.

(21) Appl. No.: 17/872,839

(22) Filed: Jul. 25, 2022

(65) Prior Publication Data
US 2022/0364967 A1 Nov. 17, 2022

Related U.S. Application Data

(63) Continuation of application No. PCT/CN2021/070061, filed on Jan. 4, 2021.

(30) Foreign Application Priority Data

Nov. 19, 2020 (CN) .......................... 202011302845.8

(51) Int. Cl.
*G01N 3/12* (2006.01)
(52) U.S. Cl.
CPC ..................................... *G01N 3/12* (2013.01)

(58) Field of Classification Search
CPC ....................................................... G01N 3/12
See application file for complete search history.

(56) References Cited

U.S. PATENT DOCUMENTS

| | | | | | |
|---|---|---|---|---|---|
| 1,332,491 | A | * | 3/1920 | Figari | ...................... G01N 3/16 |
| | | | | | 73/796 |
| 3,595,072 | A | * | 7/1971 | Richards | .................. G01N 3/00 |
| | | | | | 73/826 |

(Continued)

FOREIGN PATENT DOCUMENTS

| | | | |
|---|---|---|---|
| CN | 1296170 A | | 5/2001 |
| CN | 1107224 C | * | 4/2003 |

(Continued)

OTHER PUBLICATIONS

Internation Search Report of PCT/CN2021/070061, dated Aug. 19, 2021.

(Continued)

*Primary Examiner* — Natalie Huls

(57) ABSTRACT

An in-situ test device and method for surrounding rock strength of bolt supported roadway is provided. The test device includes a fixing mechanism, a loading mechanism, a measuring mechanism and a control system. The loading mechanism includes a hydraulic pump and a plunger pump, the hydraulic pump drives the plunger pump to work and controls the lifting speed of the loading cylinder; the measuring mechanism includes an infrared ranging unit and a wireless pressure monitoring unit; the control system controls the work of the loading mechanism and processes the monitoring data. The test device is directly installed in the roadway and fixed with the bolt. The device is loaded after leveling, the device is disassembled after the monitoring data are obtained, and the in-situ test for the surrounding (Continued)

rock strength of the bolt supported roadway is completed. The steps are simple and adaptable.

9 Claims, 13 Drawing Sheets

(56) References Cited

U.S. PATENT DOCUMENTS

| | | | | |
|---|---|---|---|---|
| 3,861,201 | A * | 1/1975 | Kaindl | G01N 33/383 73/834 |
| 4,501,153 | A * | 2/1985 | Mehes | G01N 3/08 73/803 |
| 4,538,467 | A * | 9/1985 | Stoll | G01N 33/383 73/803 |
| 9,696,229 | B2 * | 7/2017 | Schulz | G01L 25/00 |
| 11,067,488 | B1 * | 7/2021 | Zhao | G01N 3/12 |
| 11,499,897 | B2 * | 11/2022 | Yin | G01N 33/24 |
| 2021/0003490 | A1 * | 1/2021 | Zhao | G01N 3/22 |
| 2021/0223149 | A1 * | 7/2021 | Tan | G01N 3/12 |

FOREIGN PATENT DOCUMENTS

| | | | |
|---|---|---|---|
| CN | 103195425 A | | 7/2013 |
| CN | 104458420 A | * | 3/2015 |
| CN | 105716976 A | | 6/2016 |
| CN | 108444815 A | | 8/2018 |
| CN | 109187226 A | | 1/2019 |
| CN | 109490086 A | | 3/2019 |
| CN | 109765108 A | | 5/2019 |
| CN | 208934726 U | | 6/2019 |
| JP | H09189694 A | | 7/1997 |

OTHER PUBLICATIONS

Zhang, Fan, "Strength Test and Supporting Parameters Design of Roadway Surrounding Rock in Coal Mine", China Energy and Environmental Protection, vol. 42, No. 10, Oct. 31, 2020, pp. 192-195.

* cited by examiner

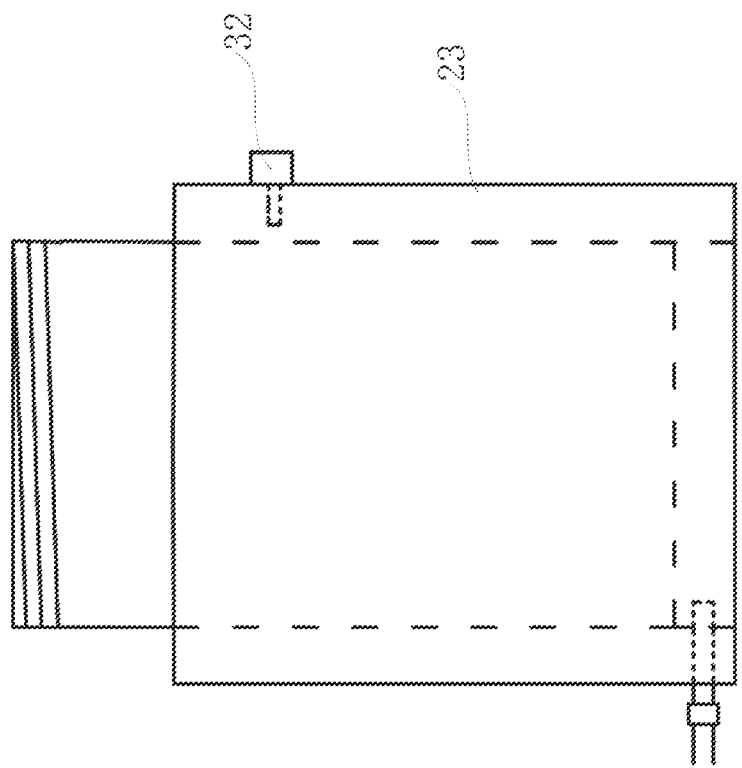

IN-SITU TEST DEVICE FOR SURROUNDING ROCK STRENGTH OF BOLT SUPPORTED ROADWAY AND METHOD THEREOF

CROSS-REFERENCE TO RELATED APPLICATIONS

This application is a continuation of International Application No. PCT/CN2021/070061 with a filing date of Jan. 4, 2021, designating the United states, and further claims to the benefit of priority from Chinese Application No. 202011302845.8 with a filing date of Nov. 19, 2020. The content of the aforementioned applications, including any intervening amendments thereto, are incorporated herein by reference.

TECHNICAL FIELD

The present disclosure relates to the field of mining engineering and measurement technology, in particular to an in-situ test device for the surrounding rock strength of a bolt supported roadway and a test method for testing using the device.

BACKGROUND

Rock mechanics parameters are the important basis for the design and selection of underground engineering support parameters, and their results directly determine the roadway support parameters of underground engineering. There are two commonly used methods for determining rock strength, namely, indoor test and in-situ test. The indoor test is to take samples underground, drill the core, and then transport it to the laboratory for the determination of rock mechanical parameters. The in-situ test is a direct measurement under the premise of small secondary disturbance to the original rock, which is closer to the relevant mechanical properties of the in-situ rock mass. The indoor test is obtained on the basis of rock sampling. When the surrounding rock of the roadway is hard, the accuracy of the test results is relatively high, but when the surrounding rock is soft, it is difficult for the rock sample coring, causing a poor applicability. The in-situ test has higher accuracy and applicability in testing the rock mass strength under two rock character conditions, which has important reference value for the support design and stability control of underground engineering.

At present, the common in-situ testing methods include hydraulic fracturing method, drilling penetration method, etc. these methods require drilling and other processes, and hydraulic fracturing method further requires high-pressure water injection, which greatly disturbs the original rock properties. In the related art, the Chinese patent (CN106680890B) provides a test device and a test method for mining hydraulic fracturing original rock stress. The test device applies the hydraulic fracturing method, which is more accurate under hard rock conditions. However, under soft rock conditions, such as sandstone or mudstone, high-pressure water injection and other processes greatly interfere with the original rock properties, resulting in significant changes in soft rock when encountering water, which has a great impact on the overall test area of this kind of surrounding rock.

Therefore, it is necessary to provide an in-situ test device and test method for the surrounding rock strength of coal mine roadway with more accurate test, wider applicability and less disturbance to surrounding rock. Especially, the accurate measurement under soft rock conditions is very important and necessary for roadway support design and surrounding rock stability analysis.

SUMMARY

In order to solve the problem of accurately measuring the strength of roadway surrounding rock, especially to adapt to the geological conditions of weak lithology, avoid the influence of drilling or water injection on surrounding rock, and make the measurement closer to the relevant mechanical properties of in-situ rock mass, the present disclosure provides a in-situ test device and a method for testing the surrounding rock strength of a bolt supported roadway. The specific technical solution is as follows.

An in-situ test device for surrounding rock strength of bolt supported roadway is provided, which includes a fixing mechanism, a loading mechanism, a measuring mechanism and a control system; the fixing mechanism includes a fixed rod, a sleeve, a fixed base, an adjusting tray and a safety ring; a plurality of through holes are arranged on the fixed base, the fixed rod is matched with any one of the through holes, the adjusting tray is arranged below the fixed base and matched with threads on the fixed rod, an periphery of the fixed base is provided with a plurality of safety rings, and the sleeve is connected with an upper end of the fixed rod and an exposed end of the anchor bolts in a roadway; the loading mechanism is configured on the fixed base, the loading mechanism includes a hydraulic pump, a plunger pump, a loading cylinder, a baseplate and a pressing die, the hydraulic pump is connected with the plunger pump through a coupling, the plunger pump is connected with a hydraulic oil tank, a high-pressure oil pipe connected with the plunger pump is respectively equipped with a speed regulating valve and a pressure relief valve; the high-pressure oil pipe is connected with the loading cylinder, and an upper end of a piston rod of the loading cylinder is fixedly provided with the baseplate, and a pressing die is installed on the baseplate; and the measuring mechanism includes an infrared ranging unit and a wireless pressure monitoring unit, wherein the infrared ranging unit is arranged on the baseplate, the wireless pressure monitoring unit is arranged on the loading cylinder, monitoring data of the measuring mechanism is transmitted to the control system, and the control system processes the monitoring data and controls the loading mechanism to work.

Preferably, a rod body at a connecting end of the fixed rod and the fixed base is provided with threads, the connecting end of the fixed rod and the sleeve is smooth, and threads inside the sleeve and an threaded end of the anchor bolt are matched with each other.

Further, the fixed base is a triangle, and the through holes on the fixed base are arranged along a center line of the triangle; a hole diameter of the through hole is larger than a diameter of the fixed rod, a nut is provided on the fixed rod below the fixed base, and a nut is arranged on the fixed base.

Further, the hydraulic pump is a direct current hydraulic pump motor driven by a direct current power supply, the direct current power supply is provided with a radio control switch; and the direct current power supply is electrically connected with the speed regulating valve and the pressure relief valve respectively.

Further, the loading cylinder is configured at a center of the fixed base, and the wireless pressure monitoring unit measures an oil pressure of hydraulic oil in the loading cylinder.

Further, the upper end of the piston rod of the loading cylinder is fixed with the baseplate through threads, the upper part of the baseplate is provided with a die mounting hole at a central position, and the baseplate is provided with a plurality of infrared ranging unit mounting holes.

Further, the control system includes a display, a wireless transmission unit, a microprocessor and an instruction unit, the instruction unit includes a plurality of control buttons, and the display and the wireless transmission unit are connected with the microprocessor.

A method for in-situ test of surrounding rock strength of bolt supported roadway, which uses the above in-situ test device for surrounding rock strength of bolt supported roadway, including the following steps:

A. determining a row space between anchor bolts of the roadway, adjusting a distance between fixed rods, connecting sleeves and the anchor bolts, and completing a configuration of the fixing mechanism, the loading mechanism and the measuring mechanism;

B. leveling the fixed base by the measuring mechanism.

C. clearing data of the control system;

D. controlling the loading mechanism to work, pressing the die stably into a wall of the roadway;

E. determining a stress-strain curve of coal and rock mass in the roadway by the control system, and stopping loading when a stress is decreased;

F. controlling a pressure relief of the loading mechanism, disassembling the fixing mechanism to complete the test.

Further, a monitoring value of stress is calculated as follows:

$$p_i = p_{i\ press}\left(\frac{d_1}{d_2}\right)^2$$

Wherein, $p_i$ is a stress value of the surrounding rock measured in the i-th test, and $p_{i\ press}$ is a pressure value measured by a pressure sensor in the i-th test, and $d_1$, $d_2$ are an inner diameter of the oil cylinder and a diameter of the pressing die respectively; and a monitoring value of strain is equal to a change value of a measured distance between the infrared ranging unit and the surrounding rock of the roadway.

Further, multiple in-situ tests of surrounding rock strength of bolt supported roadway are carried out in the same roadway, and multiple dies with different diameters are used to determine an actual surrounding rock strength of the roadway.

The present disclosure provides a device and a method for in-situ test of the surrounding rock strength of bolt supported roadway, and the advantageous effects include:

(1) The test device for in-situ test of surrounding rock strength of bolt supported roadway does not need drilling or water injection, so it has stronger adaptability to geological conditions, and the installation of the test device is more convenient, with less interference to the surrounding rock of the roadway. The measurement system of the test device converts the monitoring values of the infrared ranging unit and the wireless pressure monitoring unit into the stress and strain relationship of the surrounding rock, so that the strength of the surrounding rock of the roadway can be obtained in time.

(2) The test device makes the measurement closer to the relevant mechanical properties of the in-situ rock mass, and can be installed at the roof, two sides and other positions of the roadway to carry out the strength test of the surrounding rock. The position between the fixed rods on the fixed base can be adjusted according to the actual needs, so as to adapt to the construction conditions of different row space between anchor bolts. Therefore, the device has better adaptability.

(3) The loading mechanism can realize stable automatic loading, so as to ensure the stability of loading and reduce the test error, and the pressing die of the test device can be replaced. During the test, the model of the pressing die can be selected according to the difficulty of the pressing die entering the surrounding rock. The control system transmits signals wirelessly and controls the loading mechanism to make the measurement more convenient.

(4) By using the test device for in-situ test of surrounding rock strength in bolt supported roadway, the test method makes the test steps simpler, and the test device is easy to disassemble and install, so that the rapid and accurate measurement can be realized in the roadway. In addition, the control system can directly process data to ensure effective control loading, and the data processing is more simple. Besides, the test device and the method also have the advantages of simple structure, small volume, light weight, simple and fast operation, etc.

BRIEF DESCRIPTION OF THE DRAWINGS

FIG. 7 is the schematic diagram of the loading cylinder;

Figure 1:
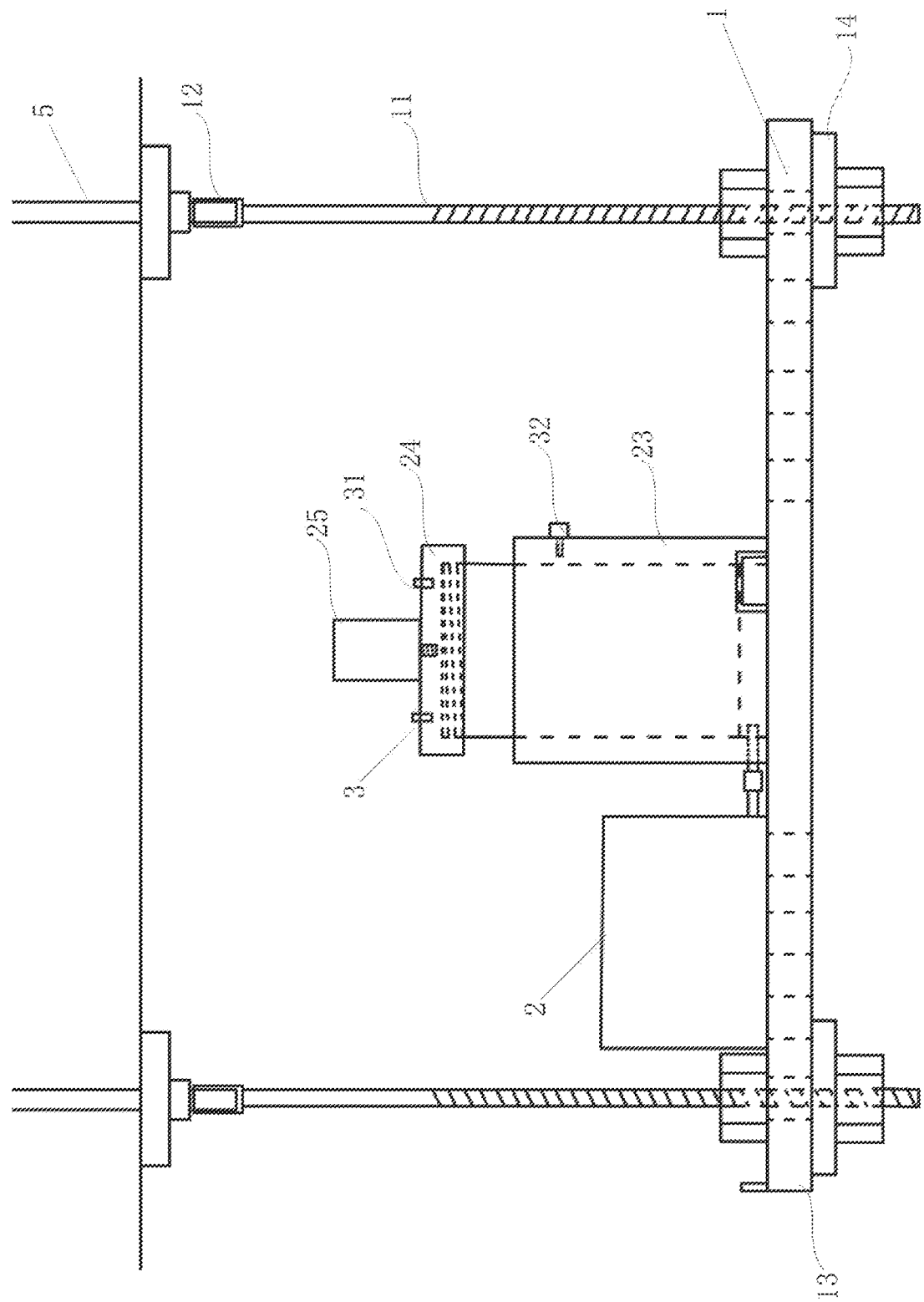
FIG. 1 is the structural diagram of the in-situ test device for the surrounding rock strength of bolt supported roadway.

Reference labels in the drawings: 1—fixing mechanism, 2—loading mechanism, 3—measuring mechanism, 4—control system; 5—anchor bolt;

11—fixed rod, 12—sleeve, 13—fixed base, 14—adjusting tray, 15—safety ring, 16—through hole, 17—nut, 18—safety rope;

21—hydraulic pump, 22—plunger pump, 23—loading cylinder, 24—baseplate, 25—pressing die, 251—die mounting hole, 26—speed regulating valve, 27—pressure relief valve, 28—oil tank, 29—power supply;

31—infrared ranging unit, 32—wireless pressure monitoring unit;

41—display, 42—wireless transmission unit, 43—microprocessor, 44—instruction unit.

DETAILED DESCRIPTION OF THE EMBODIMENTS

Figure 2:
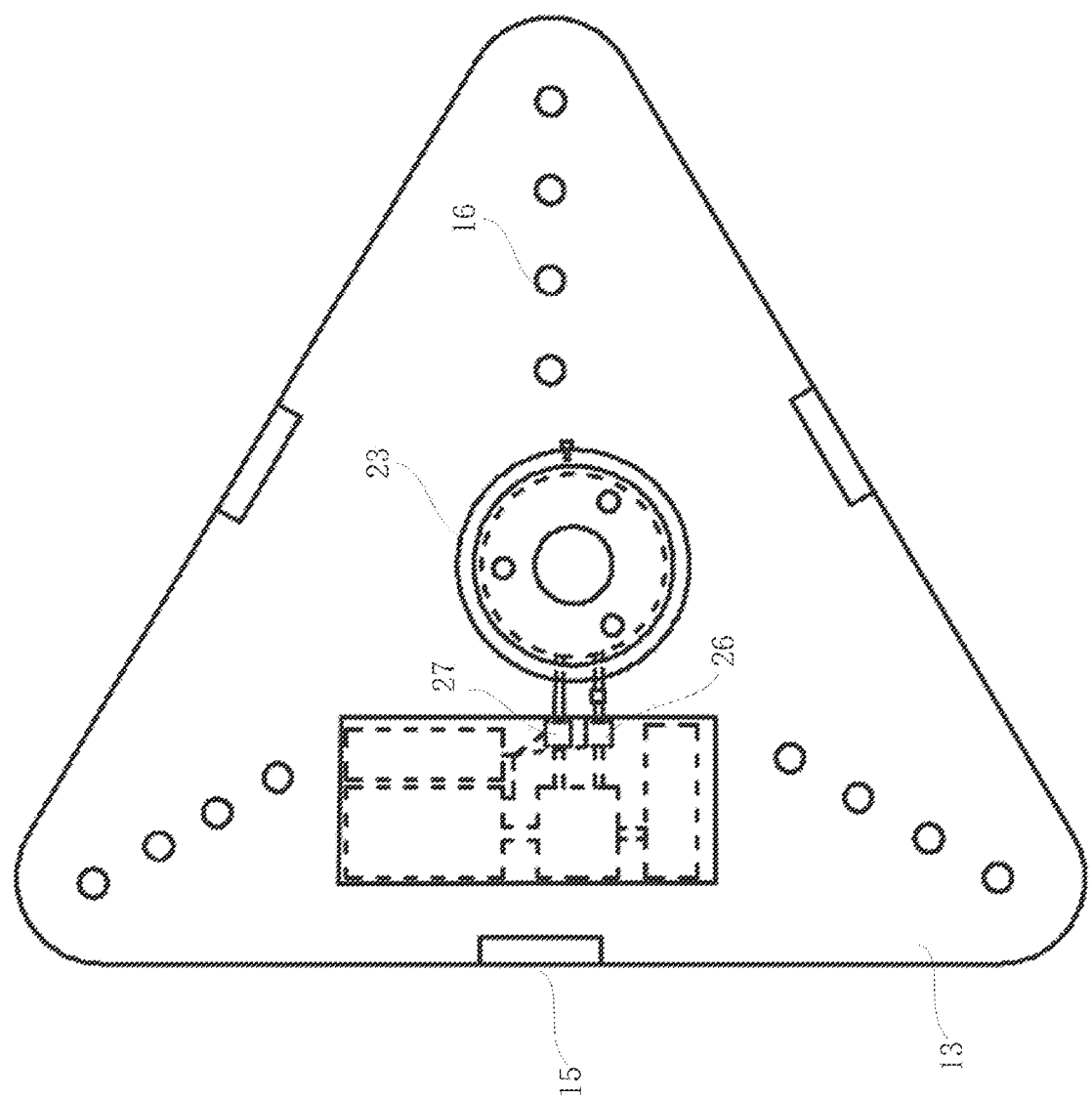
FIG. 2 is the top structural diagram of the in-situ test device for the surrounding rock strength of bolt supported roadway.
Figure 3:
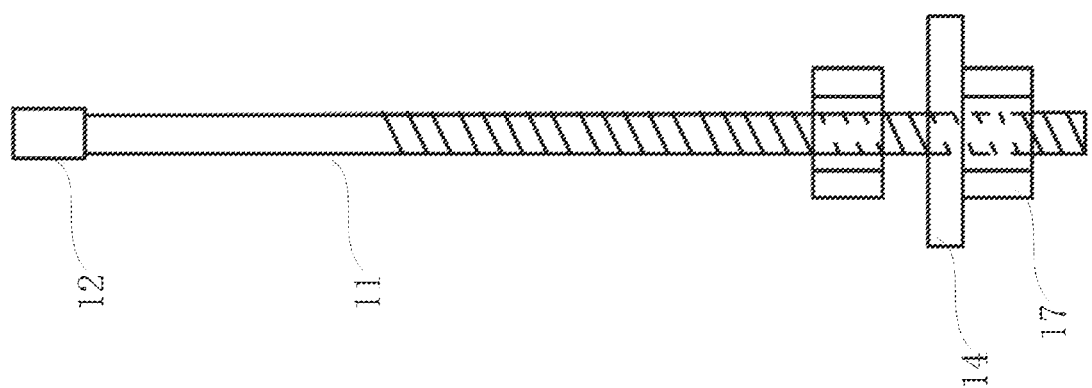
FIG. 3 is the structural diagram of the fixed rod.
Figure 4:
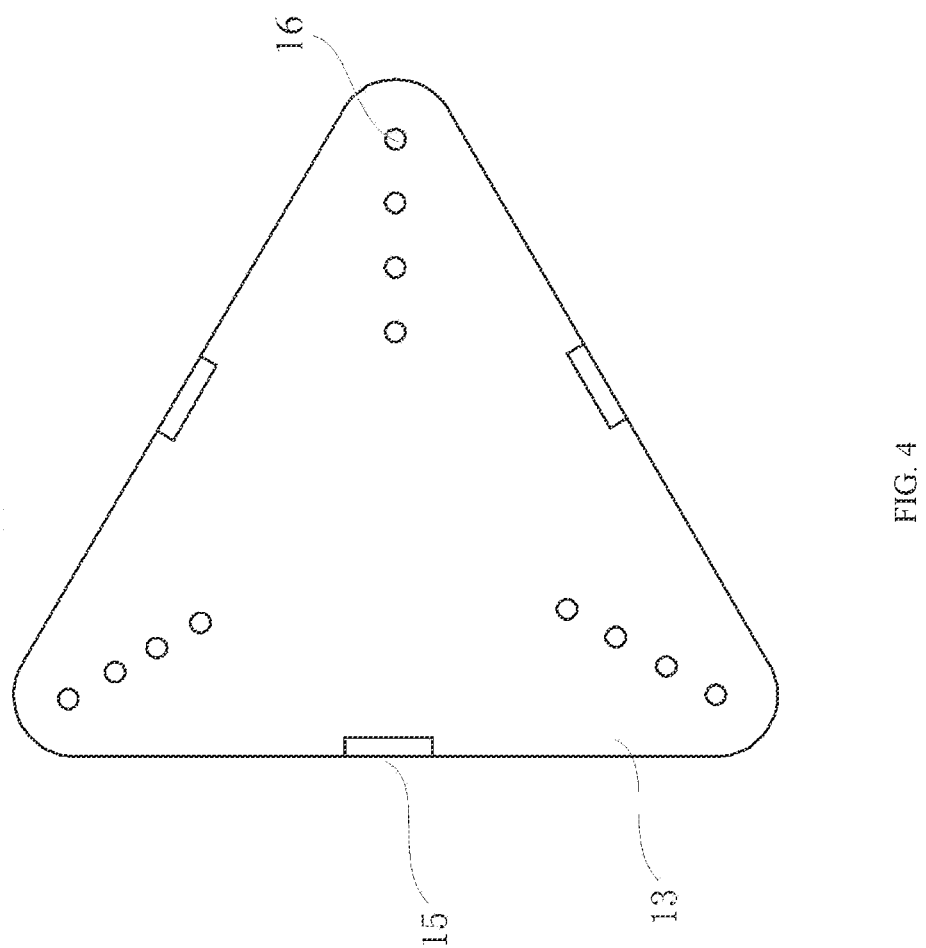
FIG. 4 is the structural diagram of the fixed base.
Figure 5:
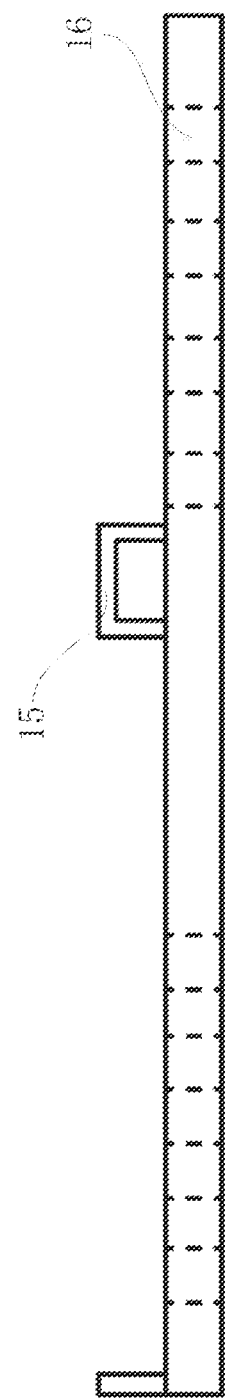
FIG. 5 is a side view structural diagram of the fixed base.
Figure 6:
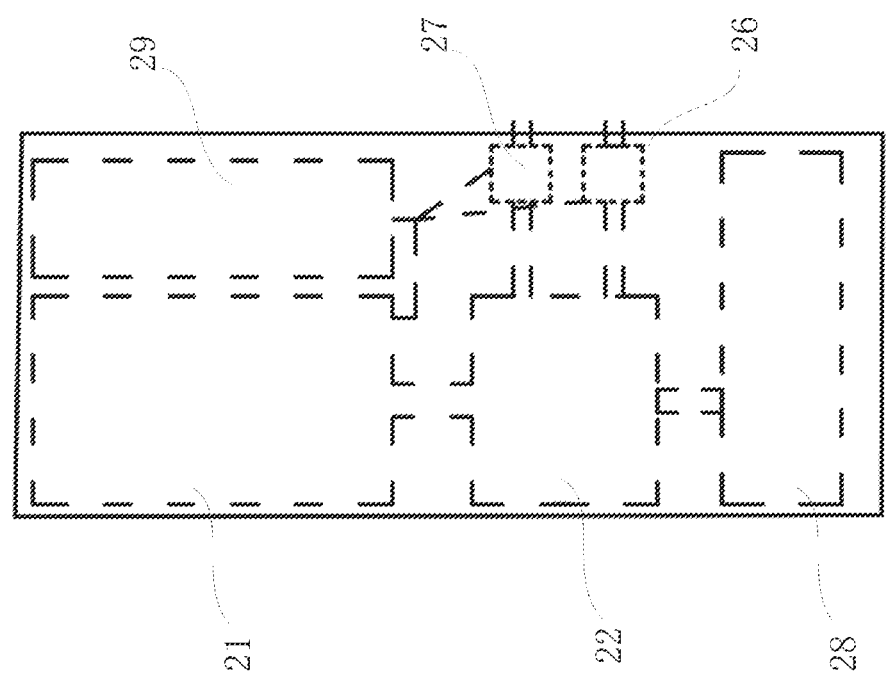
FIG. 6 is a schematic diagram of the configuration of the loading mechanism.
Figure 9:
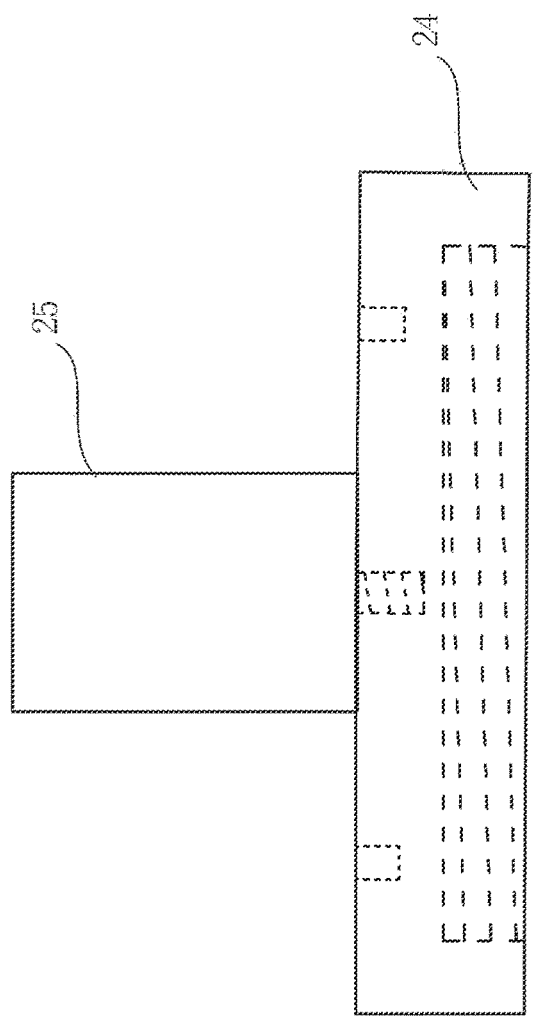
FIG. 9 is the assembly diagram of the pressing die.
Figure 8:
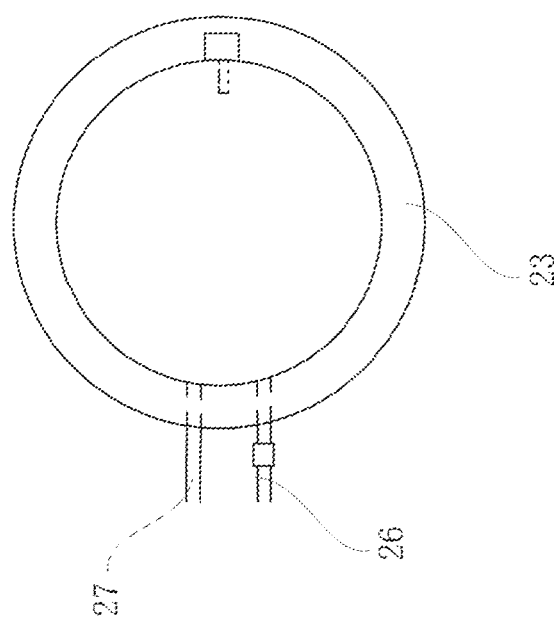
FIG. 8 is the connection diagram of the loading cylinder.
Figures 10, 11:
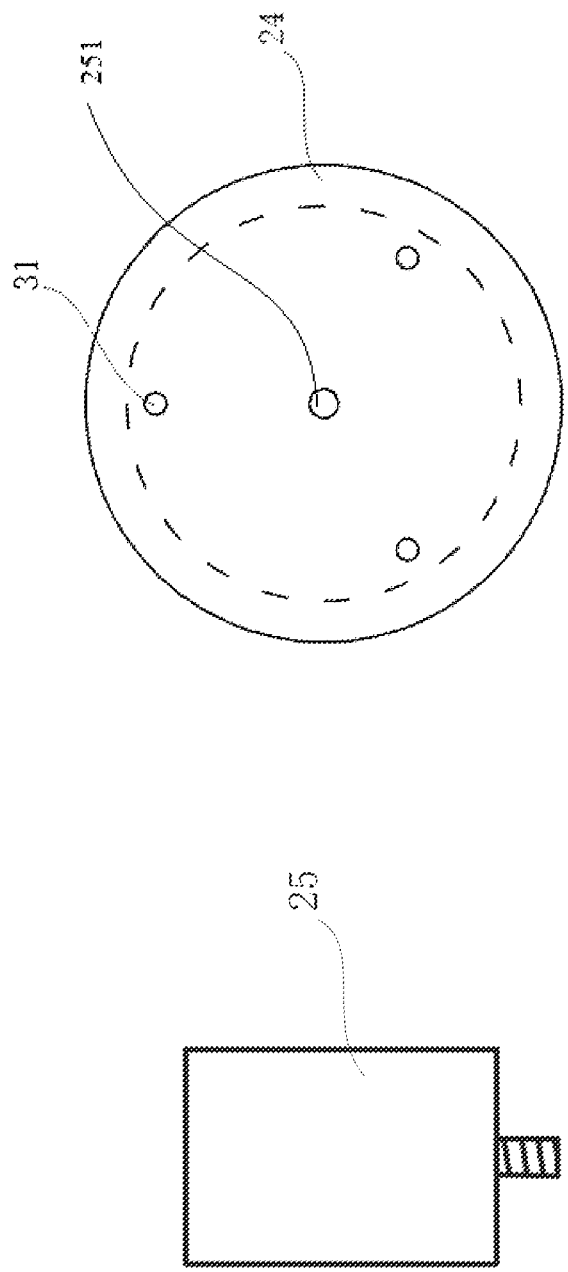
FIG. 10 is the structural diagram of the pressing die.
FIG. 11 is the layout diagram of the mounting hole of the infrared ranging unit.
Figure 12:
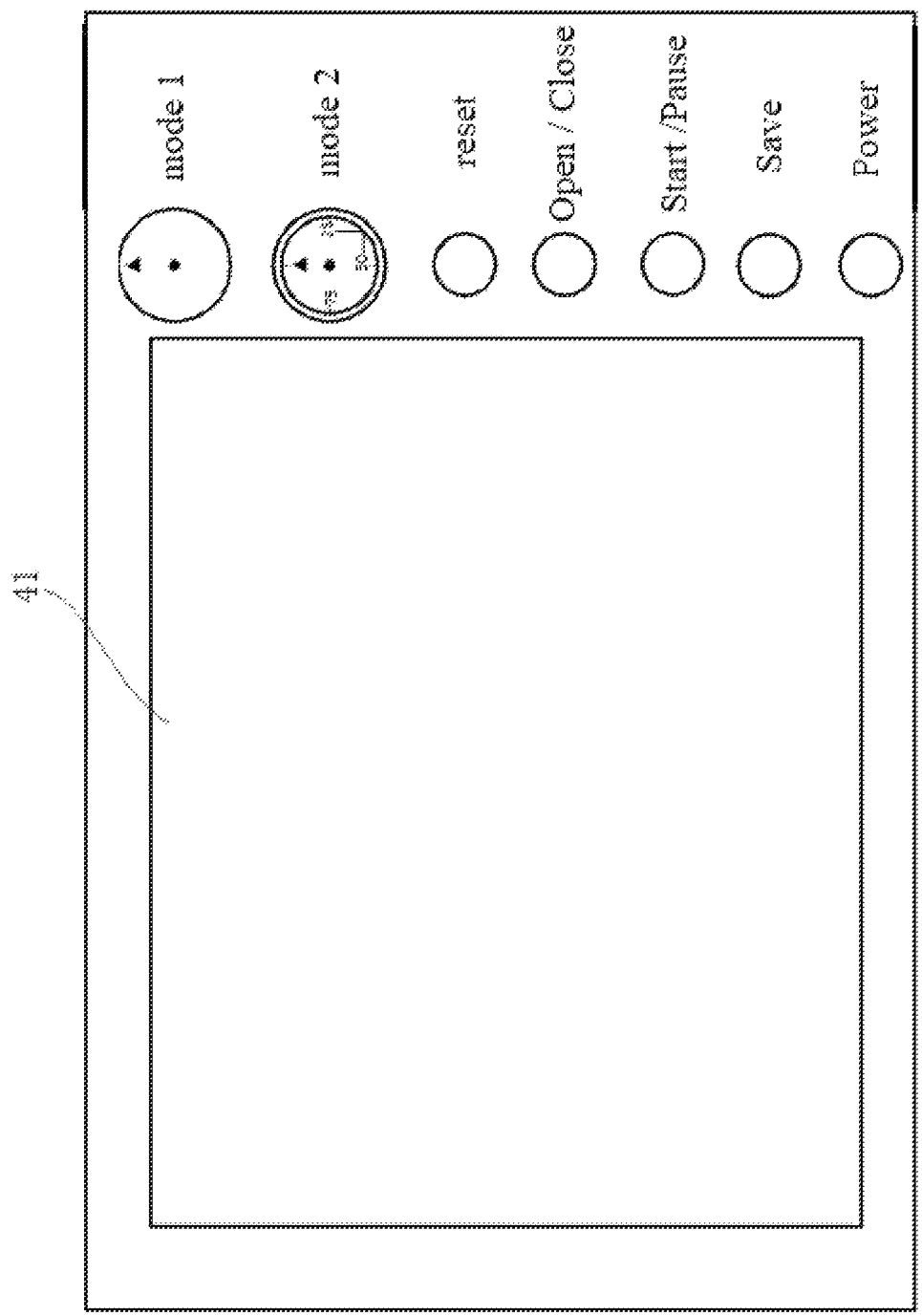
FIG. 12 is a schematic diagram of the control system.
Figure 13:
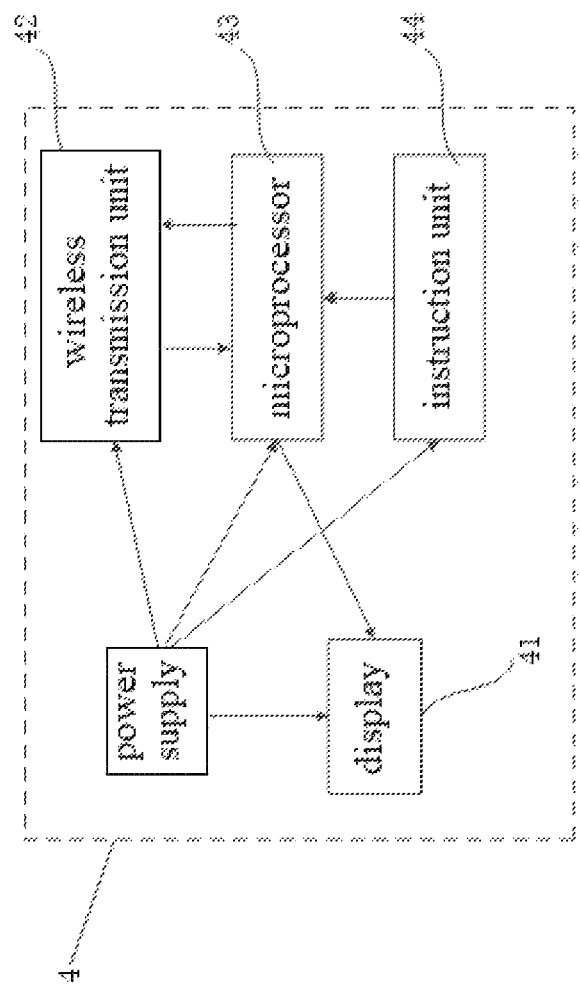
FIG. 13 is a principle diagram of the control system.
Figure 14:
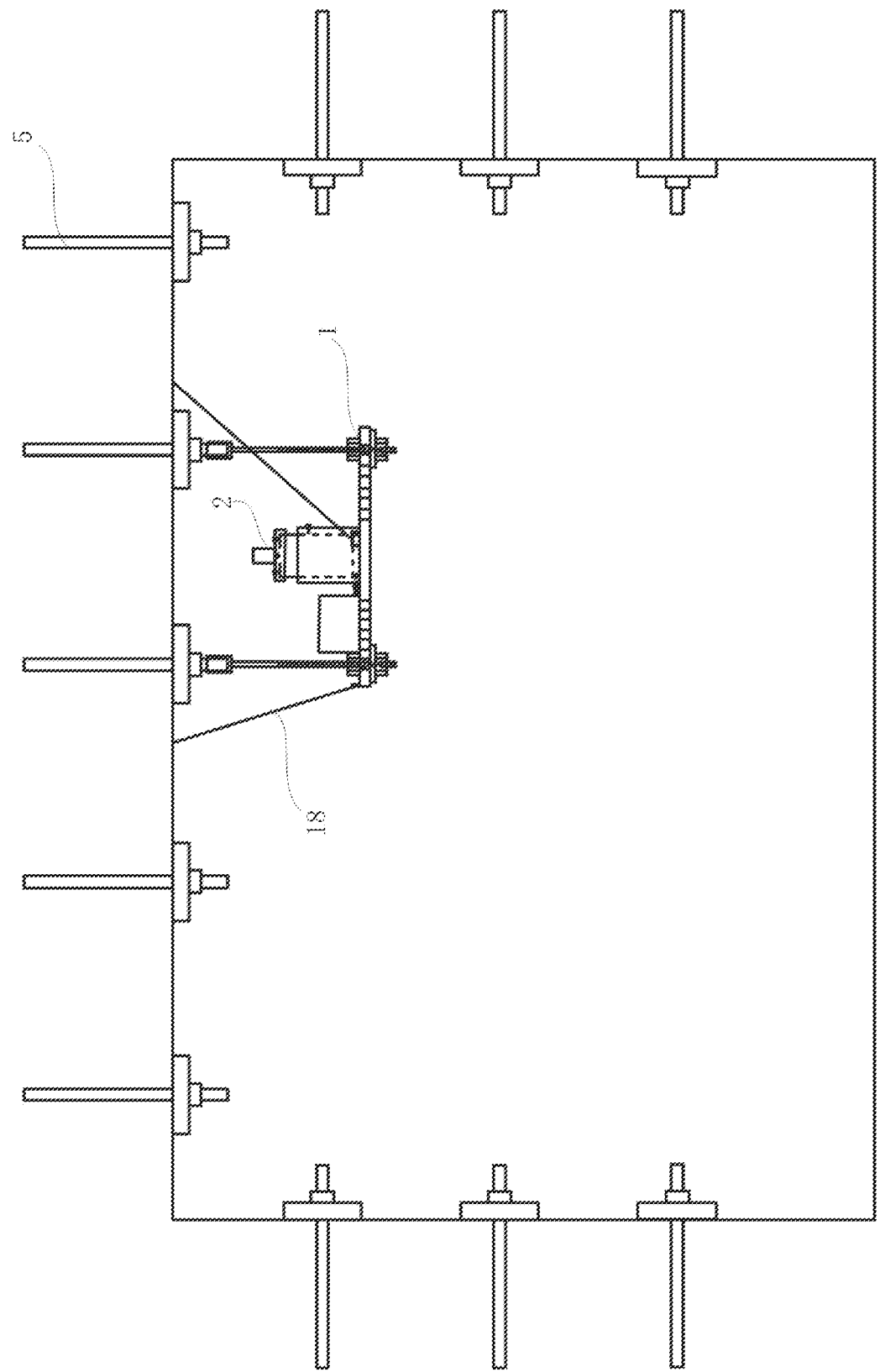
FIG. 14 is the installation structure diagram of the in-situ test device for the surrounding rock strength of bolt supported roadway.
Figure 15:
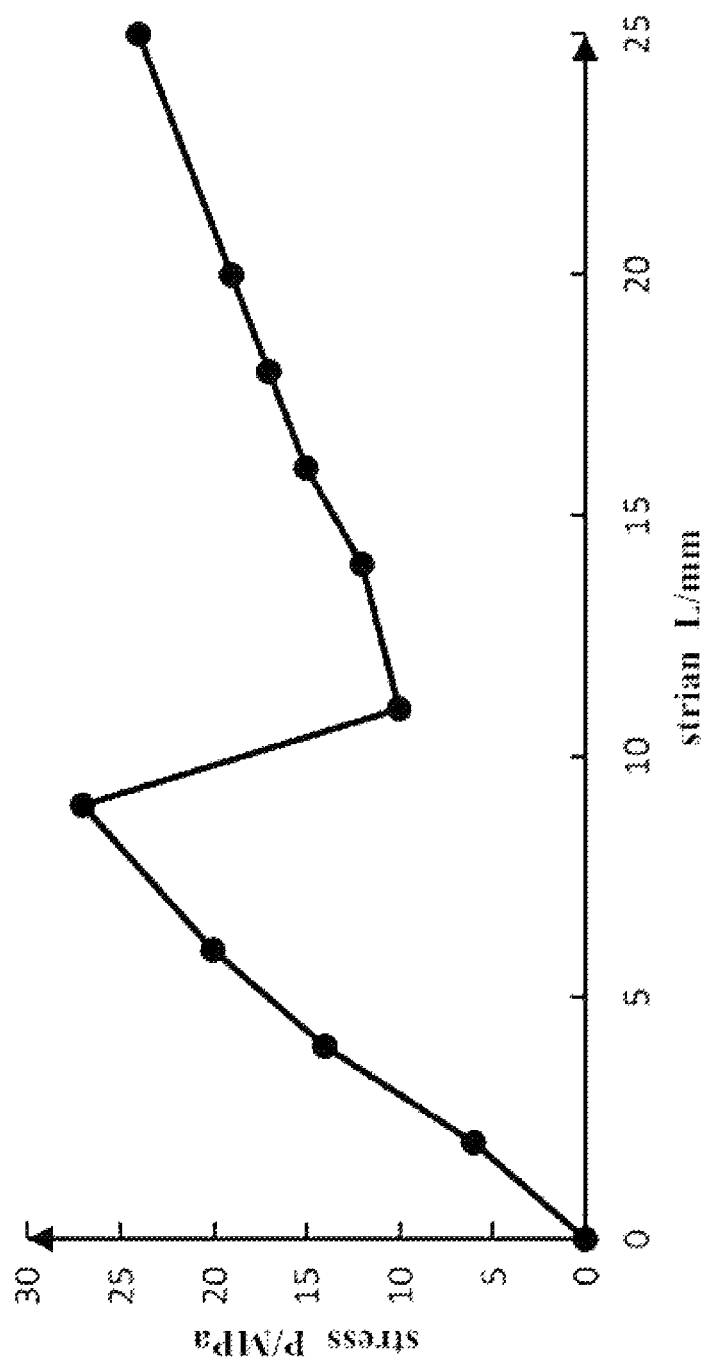
FIG. 15 is a graph of test results.

As shown in FIG. 1 to FIG. 15, the specific implementation of an in-situ test device for the surrounding rock strength of a bolt supported roadway and a test method therefor provided by the present disclosure is described as below.

Embodiment 1

An in-situ test device and test method for the surrounding rock strength of coal mine roadway with more accurate test, wider applicability and less disturbance to surrounding rock is provided, especially to achieve accurate measurement under soft rock conditions, which can effectively guide roadway support design and surrounding rock stability analysis and research.

An in-situ test device for strength of surrounding rock of bolt supported roadway, which specifically includes a fixing mechanism 1, a loading mechanism 2, a measuring mechanism 3 and a control system 4. Wherein the fixed base of the fixed mechanism is adjusted with the rise and fall of the fixed rod, so as to facilitate installation and measurement, and adapt to the construction conditions of different row space between anchor rods. The loading mechanism can realize stable automatic loading, so as to ensure the stability of loading and reduce the test error. The monitoring values of the infrared ranging unit and the wireless pressure monitoring unit are converted into the stress and strain relationship of the surrounding rock by the measuring mechanism, so that the strength of the surrounding rock of the roadway can be obtained in time. The control system controls the loading mechanism to work through wireless transmission signal, so that the measurement is more convenient.

Wherein, the fixing mechanism 1 includes a fixed rod 11, a sleeve 12, a fixed base 13, an adjusting tray 14 and a safety ring 15. A plurality of through holes 16 are arranged on the fixed base 13, which is convenient for the installation of the fixed rod 11. The fixed rod 11 is matched with any one of the through holes 16, so as to fit the space between the anchor bolts with different types. The adjusting tray 14 is arranged below the fixed base and matched with threads on the fixed rod to play a function to support and limit the fixed base. An periphery of the fixed base 13 is provided with a plurality of safety rings, and those safety rings can be used as protection when used to ensure the safety of the device. The sleeve 12 is connected with an upper end of the fixed rod and an exposed end of the anchor bolts in a roadway, so that the device can be fixed directly and is easy to install. The loading mechanism 2 is configured on the fixed base, and the structure is whole coordination to keep the center of the device stable. The loading mechanism 2 includes a hydraulic pump 21, a plunger pump 22, a loading cylinder 23, a baseplate 24 and a pressing die 25. The hydraulic pump 21 is connected with the plunger pump through a coupling, the plunger pump 22 is connected with a hydraulic oil tank 28, a high-pressure oil pipe connected with the plunger pump 22 is respectively equipped with a speed regulating valve 26 and a pressure relief valve 27. An one-way valve is arranged between the speed regulating valve 26 and the loading cylinder 23 to ensure safety of loading. The loading mechanism 2 ensures the stable loading and can flexibly controls the loading speed. The high-pressure oil pipe is connected with the loading cylinder 23, and an upper end of a piston rod of the loading cylinder 23 is fixedly provided with the baseplate 24, and a pressing die 25 is installed on the baseplate 24. The pressing die 25 has several models of fittings, specifically different models have different diameters, and the die 25 and the baseplate 24 are connected with each other through a threaded detachable connection. The measuring mechanism 3 includes an infrared ranging unit 31 and a wireless pressure monitoring unit 32, wherein the infrared ranging unit 31 is arranged on the baseplate to measure the distance between the baseplate and the surface of the surrounding rock of roadway in real-time. The wireless pressure monitoring unit 32 is arranged on the loading cylinder to monitor loading stress in real-time. The monitoring data obtained from the measuring mechanism 3 are transmitted to the control system 4, which can be wireless data transmission. The control system 4 processes the monitoring data and controls the loading mechanism to work, and the control system 4 can be configured in a handheld wireless control system.

The rod body at the connecting end of the fixed rod 11 and the fixed base 13 is provided with threads, so that it is convenient to configure nuts at the upper and lower positions of the fixed base to limit the position of the fixed base. The connecting ends of the fixed rod 11 and the sleeve 12 are smooth and can be connected by welding or interference fit. The threads inside the sleeve 12 and the threaded ends of the anchor rods are matched with each other. The fixed base is triangular, so that it is convenient to fix and determine the position of the center. The through hole on the fixed base 13 is arranged along the center line of the triangle. The hole diameter of the through hole 16 is larger than the diameter of the fixed rod, so that the installation is convenient, and the inclination of the fixed base can be regulated according to the difference of the diameter. The fixed rod under the fixed base 13 is equipped with a nut, and a nut is arranged on the upper part of the fixed base 13, so as to limit the position of the fixed base.

The hydraulic pump 21 is a direct current hydraulic pump motor and is driven by a direct current power supply. The power supply 29 is equipped with a radio control switch, and the control power supply 29 supplies power to other components. The direct current power supply is also electrically connected with the speed regulating valve and the pressure relief valve respectively. The loading cylinder 23 is arranged at the center of the fixed base to ensure the stability of the center of gravity. The wireless pressure monitoring unit 32 measures the oil pressure of the hydraulic oil in the loading cylinder. The upper end of the piston rod of the loading cylinder 23 is fixedly connected with the baseplate through threads. A die mounting hole is provided at the center above the baseplate 24. The threads in the mounting hole are matched with the threaded column on the pressing die. The baseplate is further provided with a plurality of the mounting holes of the infrared ranging unit, which can be three mounting holes of the infrared ranging unit in an isosceles triangle, and the distance is determined by calculating the average.

The control system 4 includes a display 41, a wireless transmission unit 42, a microprocessor 43 and an instruction unit 44. The instruction unit includes a plurality of control buttons. The display and the wireless transmission unit are connected with the microprocessor. The control system 4 is configured in the handheld wireless control system. The display 41, the wireless transmission unit 42, the microprocessor 43 and the instruction unit 44 are integrated on the same whole. The control knob of the instruction unit is connected to the instruction unit through the microprocessor, and the instruction unit 44 sends control signals through wireless signal transmission. The display 41 mainly displays the stress-strain curve formed by microprocessor processing, the rising speed of the hydraulic column set during the test, the monitoring value of the infrared ranging unit and the monitoring value of the wireless pressure monitoring unit.

The control system receives the monitoring values from the infrared ranging unit and the wireless pressure monitoring unit, and controls the operation state of the loading device according to the changes of the monitoring values. The microprocessor can convert the instructions sent by the instruction unit into electrical signals, and process the monitoring values from the infrared ranging unit and the wireless pressure monitoring unit to generate the stress-strain curve. After the test, the test data can be directly obtained from the control system. The control buttons include: (1) Power key, which is configured to control the power on and off of the whole system; (2) The first adjustment knob 1, which is configured to select the mode of the value measured by the infrared ranging unit set in the microprocessor, which is divided into mode 1 and mode 2, wherein mode 1 is to measure the roadway distance when the device is leveled and the value is displayed on the display; mode 2 is to convert the value into the pressing depth though the setting conversion program after loading; (3) The second adjustment knob, the function of which is to adjust the column raising speed of the loading cylinder, with the adjustment range of 0-100 mm/min; (4) Reset key, which is used to reset the average value, stress value and time value of the infrared ranging unit during the test, so as to ensure that the image on the display changes from the origin; (5) Start/pause key, which is used to control the running and stop of the loading mechanism; (6) Open/close key, which is used to control the opening and closing of the pressure relief valve. At the same time, when the pressure relief valve is opened, the rotation direction of the motor is changed, so that the plunger pump can reverse to complete the oil return function; (7) Save key, which is used to save data and images after clicking at the end of the test for exporting data for analysis.

A method for in-situ testing the strength of surrounding rock of bolt supported roadway, which uses the above-mentioned in-situ testing device for the surrounding rock strength of bolt supported roadway, and the steps include as following:

A. Determining the row space between anchor bolts of the roadway, adjusting the distance between fixed rods, connecting sleeves and the anchor bolts to complete the configuration of the fixing mechanism, the loading mechanism and the measuring mechanism. Each component of the in-situ test device for the surrounding rock strength of bolt supported roadway can be stored in the instrument box. When configuring the test device, the measuring structure is first configured at a specific position. According to the determined roadway position and the existing row space between anchor bolts, the distance between the fixed rods on the fixed base is adjusted, and the fixed base is installed on the fixed rod by using the adjusting tray and nuts.

B. Leveling the fixed base by the measuring mechanism. First, the switches of the loading mechanism, the measuring mechanism and the control system are turned on. Then, the mode 1 of the infrared ranging unit is selected through the control system, observing the measured values of the three infrared ranging units on the display. The position of the adjusting tray and the nuts on the fixed rod are adjusted according to the measured values of each infrared ranging unit, so as to adjust the position of the base until the monitored values of the three infrared ranging units are equal. After adjustment, the initial data are recorded. After leveling, the safety rope from the safety ring is connected to the anchor net or anchor bolt (cable). The safety rope can have a certain margin without tension. The safety rope is suspended and protected through the safety ring to prevent the whole device from falling.

C. Clearing data of the control system. Mode 2 of the infrared ranging unit is selected through the control system, adjusting to a preset speed through the instruction unit. Clicking the start/pause button to send the instruction to the wireless receiving device in the loading mechanism, so that the motor drives the plunger pump to start rotating. At the same time, the second adjustment knob is rotated to the preset speed, so as to open the speed regulating valve to start feeding oil into the loading cylinder at the set speed, and the loading cylinder rises. Meanwhile, the infrared ranging unit and the wireless pressure monitoring unit continuously transmit real-time data to the wireless control system. When the wireless pressure monitoring parameters in the display begin to rise significantly, the wireless transmission device sends an instruction to suspend the test, so that the motor stops rotating and the oil inlet stops. By the reset key, the stress value, the strain value and the time value on the display are reset.

D. Controlling the loading mechanism to work, pressing the pressing die stably into the wall of the roadway. After the value is cleared, the control system sends an instruction to make the motor start to rotate, continue to feed oil, the loading cylinder continues to lift the oil column, and the pressing die is gradually pressed into the wall of the roadway. With the increase of the pressing depth and the pressure in the hydraulic cylinder, the stress and the strain values of the surrounding rock of the roadway continue to increase, and the image on the display continues to rise. Until an obvious downward trend curve appears in the image, pressing the start/pause key on the control system, so that the instruction is sent to the loading mechanism to stop the motor. The second adjustment knob is turned off to stop the test, and the save key is clicked to save the data and image.

E. Determining a stress-strain curve of coal and rock mass in the roadway by the control system, and stopping loading when a stress is decreased. The data are processed and saved through the micro processing of the control system.

F. Controlling a pressure relief of the loading mechanism, and disassembling the fixing mechanism to complete the test. The control system is used to adjust the reverse rotation of the plunger pump, so as to complete the oil return, and the loading cylinder is retracted. When the monitoring parameters of the infrared ranging unit are equal to the monitoring parameters at zero set, the plunger pump is stopped to complete the oil return and start to disassemble the device.

The monitoring value of stress is calculated as follows:

$$p_i = p_{i\,press}\left(\frac{d_1}{d_2}\right)^2.$$

Wherein, $p_i$ is the stress value of the surrounding rock measured in the i-th test, and $p_{i\,press}$ is the pressure value measured by a pressure sensor in the i-th test, and $d_1$, $d_2$ are the inner diameter of the oil cylinder and the diameter of the pressing die respectively. And the monitoring value of strain is equal to the change value of the measured distance between the infrared ranging unit and the surrounding rock of the roadway. The median of the three monitoring parameters of the infrared distance measuring units is taken as the strain value of the surrounding rock. When the loading starts, the value is converted into the pressing depth through the setting program. The calculation method is: $L_i=L_{i\,begin}-L_{i\,measure}$, wherein $L_i$ is the strain value of the i-th test (unit: mm); $L_{i\,begin}$ is the average distance to the roadway at the beginning of loading of the i-th test (unit: mm); $L_{i\,measure}$ is the average distance from the i-th test to the roadway (unit: mm). In addition, the calculation method of column lifting speed is:

$$v_{column} = \frac{v_{valve}}{\pi\left(\frac{d}{2}\right)^2}.$$

Wherein, $v_{column}$ is the column lifting speed of hydraulic column, $v_{valve}$ is the oil inlet speed of electric speed regulating valve, and d is the diameter of hydraulic column.

Embodiment 2

On the basis of Embodiment 1, taking the bolt supported roadway of a mine as an example, the operation method of the device is further described in detail.

In the mine roadway, the anchor bolt adopts 2.4 m length deformed steel bar, and the end and rear parts are respectively used with fast and slow anchoring agents. The top of surrounding rock is supported by reinforcing mesh and steel guard plate, and both sides of surrounding rock are supported by metal mesh. Anchor bolts with a row space of 900 mm or 850 mm are arranged on the surface of the roadway in the vertical direction, and 5 anchor bolts are arranged in a row. 3 anchor bolts are arranged on surrounding rocks of the roadway at a spacing of 600 mm.

The specific operation steps for the test including:

(1) Selection of the test area. Because the roof of the roadway in the mine is relatively flat, and the exposed end of the anchor bolt is suitable for installing the device, the appropriate round hole is selected at the base according to the row space of the anchor bolts, so that the device can be installed conveniently.

(2) Installation of the test device. The power switch of each part of the device is turned on, the model of the pressing die is selected, the pressing die and the baseplate are installed on the upper end of the loading cylinder, the fixed rod is connected with the anchor bolts on the roadway wall respectively, fixing to the anchor bolts through the sleeve end, so as to lift the device. And the device is installed and fixed through the nuts and adjusting tray. The fixed base is leveled by the measuring mechanism, and the safety rope is connected from the safety ring to the anchor net after leveling.

(3) Selecting mode 2 to make the pressing die press into the surrounding rock of the roadway continuously, the stress-strain curve is displayed on the display, and the stress gradually increases. During this period, the curve fluctuates slightly until the curve reaches the peak point, and there is an obvious downward trend. At this time, stop the test, adjust the second adjustment knob to make the column raising speed to 0, and click the start/pause key and save key to save the test data and images.

(4) Control the loading cylinder for pressure relief and disassemble the test device.

the test is continued and the above operations are repeated, replacing the position where the fixed rod passes through the round hole or reselect other test areas, selecting the model of pressing die. And multiple tests is conducted until the end of the test. After that, the fixed rod and other components are removed, the power supply of each component is disconnected, and then the device is putted back into the instrument box.

In this embodiment, according to the curve obtained from the test, the stress rises steadily at first, and shows an obvious downward trend when reaching a certain value, and then continues to rise slowly. The stress at the turning point is 27 MPa, that is, the measured compressive strength of the surrounding rock of the test roadway is 27 MPa.

It should be appreciated that the foregoing is only preferred embodiments of the invention and is not for use in limiting the invention. Although this invention is described in detail based on the foregoing preferred embodiments, it is apparent for those skilled in the art that modification of technical proposals or equivalent substitution of part or all of the technical features can be made. Any modification, equivalent substitution, and improvement without departing from the spirit and principle of this invention should be covered in the protection scope of the invention.

What is claimed is:

1. A method for in-situ test of surrounding rock strength of bolt supported roadway, wherein an in-situ test device for surrounding rock strength of bolt supported roadway is used, which comprises a fixing mechanism, a loading mechanism, a measuring mechanism and a control system;

the fixing mechanism comprises fixed rods, sleeves, a fixed base, an adjusting tray and a safety ring; a plurality of through holes are arranged on the fixed base, each of the fixed rods is matched with any one of the through holes, the adjusting tray is arranged below the fixed base and matched with threads on each of the fixed rods, a periphery of the fixed base is provided with a plurality of safety rings, and each of the sleeves is connected with an upper end of each of the fixed rods and an exposed end of anchor bolts in a roadway;

the loading mechanism is configured on the fixed base, the loading mechanism comprises a hydraulic pump, a plunger pump, a loading cylinder, a baseplate and a pressing die, the hydraulic pump is connected with the plunger pump through a coupling, the plunger pump is connected with a hydraulic oil tank, a high-pressure oil pipe connected with the plunger pump is respectively equipped with a speed regulating valve and a pressure relief valve; the high-pressure oil pipe is connected with the loading cylinder, and an upper end of a piston rod of the loading cylinder is fixedly provided with the baseplate, and a pressing die is installed on the baseplate;

the measuring mechanism comprises an infrared ranging unit and a wireless pressure monitoring unit, wherein the infrared ranging unit is arranged on the baseplate, the wireless pressure monitoring unit is arranged on the loading cylinder, monitoring data of the measuring mechanism is transmitted to the control system, and the control system processes the monitoring data and controls the loading mechanism to work;

the method comprises following steps:

A. determining a row space between the anchor bolts of the roadway, adjusting a distance between the fixed rods, connecting the sleeves to the anchor bolts, and completing a configuration of the fixing mechanism, the loading mechanism and the measuring mechanism;

B. leveling the fixed base by the measuring mechanism;

C. clearing data of the control system;

D. controlling the loading mechanism to work, pressing the die stably into a wall of the roadway;

E. determining a stress-strain curve of coal and rock mass in the roadway by the control system, and stopping loading when a stress is decreased; and F. controlling a pressure relief of the loading mechanism, disassembling the fixing mechanism to complete the test.

2. The method for in-situ test of surrounding rock strength of bolt supported roadway according to claim 1, wherein a rod body at a connecting end of each of the fixed rods and the fixed base is provided with threads, the connecting end of each of the fixed rods and a connecting end of each of the sleeves are smooth, and threads inside each of the sleeves and a threaded end of each of the anchor bolts are matched with each other.

3. The method for in-situ test of surrounding rock strength of bolt supported roadway according to claim 1, wherein the fixed base is a triangle, and the through holes on the fixed base are arranged along a center line of the triangle; a hole diameter of each of the through holes is larger than a diameter of each of the fixed rods, nuts are respectively provided on each of the fixed rods below the fixed base and provided on the fixed base.

4. The method for in-situ test of surrounding rock strength of bolt supported roadway according to claim 1, wherein the hydraulic pump is a direct current hydraulic pump motor driven by a direct current power supply, the direct current power supply is provided with a radio control switch; and the direct current power supply is electrically connected with the speed regulating valve and the pressure relief valve respectively.

5. The method for in-situ test of surrounding rock strength of bolt supported roadway according to claim 1, wherein the loading cylinder is configured at a center of the fixed base, and the wireless pressure monitoring unit measures an oil pressure of hydraulic oil in the loading cylinder.

6. The method for in-situ test of surrounding rock strength of bolt supported roadway according to claim 5, wherein the upper end of the piston rod of the loading cylinder is fixed with the baseplate through threads, the upper part of the baseplate is provided with a die mounting hole at a central position, and the baseplate is provided with a plurality of infrared ranging unit mounting holes.

7. The method for in-situ test of surrounding rock strength of bolt supported roadway according to claim 1, wherein the control system comprises a display, a wireless transmission unit, a microprocessor and an instruction unit, the instruction unit comprises a plurality of control buttons, and the display and the wireless transmission unit are connected with the microprocessor.

8. The method for in-situ test of surrounding rock strength of bolt supported roadway according to claim 1, wherein a monitoring value of stress is calculated as follows:

$$p_i = p_{i\,press}\left(\frac{d_1}{d_2}\right)^2$$

wherein, $p_i$ is a stress value of the surrounding rock measured in the i-th test, and $p_{i\,press}$ is a pressure value measured by a pressure sensor in the i-th test, and $d_1$, $d_2$ are an inner diameter of the loading cylinder and a diameter of the pressing die respectively;

a monitoring value of strain is equal to a change value of a measured distance between the infrared ranging unit and the surrounding rock of the roadway.

9. The method for in-situ test of surrounding rock strength of bolt supported roadway according to claim 8, wherein multiple in-situ tests of surrounding rock strength of bolt supported roadway are carried out in the same roadway, and multiple dies with different diameters are used to determine an actual surrounding rock strength of the roadway.

* * * * *